United States Patent
Mizumoto

(10) Patent No.: US 10,925,821 B2
(45) Date of Patent: Feb. 23, 2021

(54) METHOD FOR PRODUCING LIQUID COMPOSITION FOR ORAL CAVITY AND LIQUID COMPOSITION FOR ORAL CAVITY

(71) Applicant: KAO CORPORATION, Tokyo (JP)

(72) Inventor: Takeshi Mizumoto, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/539,753

(22) PCT Filed: Dec. 22, 2015

(86) PCT No.: PCT/JP2015/085885
§ 371 (c)(1),
(2) Date: Jun. 26, 2017

(87) PCT Pub. No.: WO2016/104536
PCT Pub. Date: Jun. 30, 2016

(65) Prior Publication Data
US 2017/0367951 A1  Dec. 28, 2017

(30) Foreign Application Priority Data
Dec. 26, 2014  (JP) .............................. JP2014-264055

(51) Int. Cl.
| | | |
|---|---|---|
| *A61K 8/34* | (2006.01) | |
| *A61K 8/365* | (2006.01) | |
| *A61K 8/63* | (2006.01) | |
| *A61Q 11/00* | (2006.01) | |
| *A61K 8/49* | (2006.01) | |
| *A61K 31/19* | (2006.01) | |
| *A61K 8/40* | (2006.01) | |
| *A61K 8/92* | (2006.01) | |
| *A61K 36/484* | (2006.01) | |
| *A61K 45/06* | (2006.01) | |
| *A61K 8/9789* | (2017.01) | |
| *A61K 8/9794* | (2017.01) | |

(52) U.S. Cl.
CPC .............. *A61K 8/345* (2013.01); *A61K 8/365* (2013.01); *A61K 8/40* (2013.01); *A61K 8/4926* (2013.01); *A61K 8/63* (2013.01); *A61K 8/922* (2013.01); *A61K 8/9789* (2017.08); *A61K 8/9794* (2017.08); *A61K 31/19* (2013.01); *A61K 36/484* (2013.01); *A61K 45/06* (2013.01); *A61Q 11/00* (2013.01); *A61K 2800/262* (2013.01)

(58) Field of Classification Search
CPC .... A61K 8/345; A61K 8/9794; A61K 8/9789; A61K 8/365; A61K 8/40; A61K 8/4926; A61K 8/63; A61K 8/922; A61K 31/19; A61K 36/484; A61K 45/06; A61K 2800/262; A61Q 11/00
USPC ........................................................ 424/55
See application file for complete search history.

(56) References Cited

U.S. PATENT DOCUMENTS 8,673,271 B2 * 3/2014 Kato ........................ A61K 8/19
424/49

FOREIGN PATENT DOCUMENTS

| JP | 2011-144160 A | 7/2011 |
|---|---|---|
| JP | 2011-168557 A | 9/2011 |
| JP | 2012-148998 A | 8/2012 |
| JP | 2013-75860 A | 4/2013 |
| JP | 2013-203735 A | 10/2013 |
| JP | 2014-62074 A | 4/2014 |
| JP | 2014-185126 A | 10/2014 |

OTHER PUBLICATIONS

International Search Report dated Feb. 16, 2016, in PCT/JP2015/085885, filed Dec. 22, 2015.
Extended European Search Report dated Jun. 27, 2018 in European Patent Application No. 15873104.2, 8 pages.

* cited by examiner

*Primary Examiner* — Adam C Milligan
(74) *Attorney, Agent, or Firm* — Oblon, McClelland, Maier & Neustadt, L.L.P.

(57) ABSTRACT

The present invention relates to a method for producing a liquid composition for oral cavity in which β-glycyrrhetinic acid is stably dispersed or dissolved to exhibit an increased transparency and which also can ensure a sufficient amount of β-glycyrrhetinic acid adsorbed on gingiva, even if the amount of a cationic surfactant or an anionic surfactant is restricted; and such a liquid composition for oral cavity. Specifically, the present invention relates to a method for producing a liquid composition for oral cavity, comprising the following step 1 to step 4: (Step 1) a step of blending water (F) with an organic acid and a salt thereof (E) to adjust the pH of a resultant mixture to 5 or more and 6.8 or less, (Step 2) a step of blending 0.02% by mass or more and 0.1% by mass or less of cetylpyridinium chloride (B) into the mixture, (Step 3) a step of blending 0.02% by mass or more and 0.1% by mass or less of β-glycyrrhetinic acid (A) and 2% by mass or more and 10% by mass or less of propylene glycol (C) into the mixture, and (Step 4) a step of blending 0.45% by mass or more and 1.1% by mass or less of polyoxyethylene hydrogenated castor oil (D) into the mixture, wherein the component (A) and the component (B) are blended at a specific mass ratio, and these steps are carried out in a specific order.

13 Claims, No Drawings

METHOD FOR PRODUCING LIQUID COMPOSITION FOR ORAL CAVITY AND LIQUID COMPOSITION FOR ORAL CAVITY

CROSS REFERENCE TO RELATED APPLICATION

This application is a national stage entry under 35 USC 371 of PCT/JP2015/085885 filed on Dec. 22, 2015, and claims priority to Japanese Patent Application No. 2014-264055 filed on Dec. 26, 2014.

FIELD OF THE INVENTION

The present invention relates to a method for producing a liquid composition for oral cavity, and a liquid composition for oral cavity.

BACKGROUND OF THE INVENTION

β-Glycyrrhetinic acid is a substance which is obtained by hydrolyzing glycyrrhizic acid obtained from licorice. This substance is an oil-soluble active ingredient providing an anti-inflammatory action, and has also been known as a poorly water-soluble substance.

For example, Patent Literature 1 describes a composition for oral cavity that is produced by blending a specific amount of glycyrrhetinic acid with an oily base, and further blending calcium hydrogen phosphate, which is powder having a high oil absorption, to thereby stabilize preparations. Moreover, Patent Literature 2 describes a dentifrice composition produced by blending β-glycyrrhetinic acid with sodium chloride and polyoxyethylene hydrogenated castor oil at a specific mass ratio, and further blending heavy calcium carbonate and phellodendron bark extract into the mixture, to thereby enhance the stability of β-glycyrrhetinic acid.

On the other hand, Patent Literature 3 describes a composition for oral cavity produced by blending glycyrrhetinic acid, polyoxyethylene hydrogenated castor oil, N-acyl basic amino acid alkyl ester or salts thereof, and oily components other than glycyrrhetinic acid at a specific mass ratio, to thereby enhance the solubility or dispersion stability of glycyrrhetinic acid. Furthermore, Patent Literature 4 describes a liquid composition for oral cavity comprising specific amounts of β-glycyrrhetinic acid, allantoin, and a nonionic surfactant, and having a pH value of 4.5 to 6.

(Patent Literature 1) JP-A-2011-144160
(Patent Literature 2) JP-A-2012-148998
(Patent Literature 3) JP-A-2014-62074
(Patent Literature 4) JP-A-2011-168557

SUMMARY OF THE INVENTION

The present invention relates to a method for producing a liquid composition for oral cavity, comprising the following step 1 to step 4:

(Step 1) a step of blending water (F) with an organic acid and a salt thereof (E) to adjust the pH of a resultant mixture at 25° C. to 5 or more and 6.8 or less, (Step 2) a step of blending 0.01% by mass or more and 0.1% by mass or less of cetylpyridinium chloride (B) into the mixture, (Step 3) a step of blending 0.02% by mass or more and 0.1% by mass or less of β-glycyrrhetinic acid (A) and 2% by mass or more and 10% by mass or less of propylene glycol (C) into the mixture, and (Step 4) a step of blending 0.4% by mass or more and 1.1% by mass or less of polyoxyethylene hydrogenated castor oil (D) into the mixture, wherein a mass ratio between the component (A) and the component (B), ((A)/(B)), is 0.3 or more and 1.3 or less, after completion of the step 1, the step 2 and the step 3 are simultaneously carried out, or the step 2 is carried out, followed by carrying out the step 3, and the step 4 and any one of the steps 1 to 3 are simultaneously carried out, or the step 4 is carried out independently from the steps 1 to 3.

Moreover, the present invention relates to a method for producing a liquid composition for oral cavity, which comprises blending the following components (A) to (F):

(A) 0.02% by mass or more and 0.1% by mass or less of β-glycyrrhetinic acid,
(B) 0.01% by mass or more and 0.1% by mass or less of cetylpyridinium chloride,
(C) 2% by mass or more and 10% by mass or less of propylene glycol,
(D) 0.4% by mass or more and 1.1% by mass or less of polyoxyethylene hydrogenated castor oil,
(E) an organic acid and a salt thereof, and
(F) 70% by mass or more and 97% by mass or less of water, the composition having a pH at 25° C. of 5 or more and 6.8 or less, and a mass ratio between the component (A) and the component (B), ((A)/(B)), of 0.3 or more and 1.3 or less, wherein the component (B) and the component (A) are simultaneously blended, or the component (B) is blended before the component (A) is blended.

Furthermore, the present invention relates to a liquid composition for oral cavity, comprising the following components (A) to (F):

(A) 0.02% by mass or more and 0.1% by mass or less of β-glycyrrhetinic acid,
(B) 0.01% by mass or more and 0.1% by mass or less of cetylpyridinium chloride,
(C) 2% by mass or more and 10% by mass or less of propylene glycol,
(D) 0.4% by mass or more and 1.1% by mass or less of polyoxyethylene hydrogenated castor oil,
(E) an organic acid and a salt thereof, and
(F) 70% by mass or more and 97% by mass or less of water, wherein the pH of the liquid composition at 25° C. is 5 or more and 6.8 or less, a mass ratio between the component (A) and the component (B), ((A)/(B)), is 0.3 or more and 1.3 or less, and the liquid composition is transparent or semi-transparent.

Upon attempting to obtain a liquid composition for oral cavity in which β-glycyrrhetinic acid is stably dispersed or dissolved, if powder having a high oil absorption, such as calcium hydrogen phosphate or heavy calcium carbonate, is blended, as described in Patent Literature 1 or Patent Literature 2, the powder itself is not dissolved in water and is not favorably dispersed therein, whereby it is difficult to ensure stable uniformity or transparency. Thus, the means of allowing β-glycyrrhetinic acid to adsorb on powder having a high oil absorption is not necessarily effective.

On the other hand, as described in Patent Literatures 3 and 4, when a cationic surfactant such as N-acyl basic amino acid alkyl ester or a salt thereof, or allantoin or a salt thereof, is used in combination, it is necessary to consider irritation or flavor of such a substance, and also, the amount thereof is restricted. Thus, in order to increase the content of glycyrrhetinic acid and also enhance transparency and the like, further improvement is required. Moreover, even if a nonionic surfactant is used in combination, the amount of β-glycyrrhetinic acid adsorbed on gingiva is likely to be decreased, as the amount of the nonionic surfactant is increased.

Accordingly, the present invention relates to a method for producing a liquid composition for oral cavity in which β-glycyrrhetinic acid is stably dispersed or dissolved to exhibit an increased transparency and which also can ensure a sufficient amount of β-glycyrrhetinic acid adsorbed on gingiva, even if the amount of a cationic surfactant or an anionic surfactant is restricted; and such a liquid composition for oral cavity.

Hence, the present inventor has conducted various studies. As a result, the inventor has found that when adjusting the pH to a specific value, and blending β-glycyrrhetinic acid, a cationic bactericide, propylene glycol, an organic acid and a salt thereof, and polyoxyethylene hydrogenated castor oil through specific steps, an increased amount of β-glycyrrhetinic acid can be stably dispersed or dissolved, to thereby obtain a liquid composition which has high transparency while ensuring the amount of the β-glycyrrhetinic acid adsorbed on gingiva.

According to the present invention, a liquid composition for oral cavity which is capable of stably dispersing or dissolving β-glycyrrhetinic acid therein, has high transparency, and provides good feeling of use, can be obtained.

DETAILED DESCRIPTION OF THE INVENTION

Hereinafter, the present invention will be described in detail.

The liquid composition for oral cavity of the present invention comprises, as a component (A), 0.02% by mass or more and 0.1% by mass or less of β-glycyrrhetinic acid. β-Glycyrrhetinic acid has anti-inflammatory action, alveolar bone resorption-inhibiting action, histamine release-inhibiting action and the like, and it exhibits an effect of preventing or ameliorating periodontitis, periodontal disease, etc., by being blended into the liquid composition for oral cavity. The β-glycyrrhetinic acid is 3β-hydroxy-11-oxooleana-12-ene-30-carboxylic acid, which is obtained by hydrolyzing glycyrrhizic acid obtained from licorice or the like.

Even in a case where the after-mentioned nonionic surfactant used as a component (D), or other cationic surfactants or anionic surfactants are present in the liquid composition for oral cavity, in view of ensuring the adsorptivity of the component (A) on gingiva, the content of the component (A) is 0.02% by mass or more, preferably 0.025% by mass or more, in the liquid composition for oral cavity of the present invention. On the other hand, in view of preventing the turbidity or precipitate in the liquid composition for oral cavity, the content of the component (A) is 0.1% by mass or less, preferably 0.08% by mass or less, further preferably 0.05% by mass or less, in the liquid composition for oral cavity of the present invention. Moreover, the content of the component (A) is 0.02% by mass or more and 0.1% by mass or less, preferably 0.02% by mass or more and 0.08% by mass or less, more preferably 0.025% by mass or more and 0.05% by mass or less, in the liquid composition for oral cavity of the present invention.

The liquid composition for oral cavity of the present invention comprises, as a component (B), 0.01% by mass or more and 0.1% by mass or less of cetylpyridinium chloride. The component (B) is a water-soluble bactericide, and when the liquid composition for oral cavity comprises the component (B) as well as the component (A), the component (B) prevents the precipitation of the component (A) and the white turbidity of the liquid composition for oral cavity to ensure stable uniformity and transparency. In view of sufficient pharmacological action and the stability of the component (A), the content of the component (B) is 0.01% by mass or more, preferably 0.02% by mass or more, more preferably 0.03% by mass or more, in the liquid composition for oral cavity of the present invention. On the other hand, in view of flavor and suppressing bitter taste, the content of the component (B) is 0.1% by mass or less, preferably 0.08% by mass or less, more preferably 0.07% by mass or less, in the liquid composition for oral cavity of the present invention. Moreover, the content of the component (B) is 0.01% by mass or more and 0.1% by mass or less, preferably from 0.02% to 0.08% by mass, more preferably from 0.03% to 0.07% by mass, in the liquid composition for oral cavity of the present invention.

In view of the stability of the component (A) and preventing generation of precipitates, a mass ratio of the content of the component (A) and the content of the component (B), ((A)/(B)), is 1.3 or less, preferably 1.1 or less, more preferably 1 or less. On the other hand, in view of allowing the component (A) to sufficiently exhibit its pharmacological action, the mass ratio ((A)/(B)) is 0.3 or more, preferably 0.4 or more. Moreover, in view of the stability of the component (A), the mass ratio of the content of the component (A) and the content of the component (B), ((A)/(B)), is 0.3 or more and 1.3 or less, preferably from 0.4 to 1.1, more preferably from 0.4 to 1.

The liquid composition for oral cavity of the present invention comprises, as a component (C), 2% by mass or more and 10% by mass or less of propylene glycol. In view of the stability of the component (A) in the liquid composition for oral cavity, the content of the component (C) is 2% by mass or more, preferably 3% by mass or more, in the liquid composition for oral cavity of the present invention. On the other hand, in view of flavor, the content of the component (C) is 10% by mass or less, preferably 8% by mass or less, in the liquid composition for oral cavity of the present invention. Moreover, the content of the component (C) is 2% by mass or more and 10% by mass or less, preferably from 3% to 8% by mass, in the liquid composition for oral cavity of the present invention.

In view of the stability of the component (A) in the liquid composition for oral cavity, the mass ratio between the content of the component (C) and the content of the component (A), ((C)/(A)), is preferably 40 or more, more preferably 50 or more, further preferably 60 or more. In view of flavor, the mass ratio ((C)/(A)) is preferably 500 or less, more preferably 300 or less, further preferably 250 or less.

The liquid composition for oral cavity of the present invention comprises, as a component (D), 0.4% by mass or more and 1.1% by mass or less of polyoxyethylene hydrogenated castor oil. In view of ensuring the solubility or dispersibility of the component (A) while using the component (A) in combination with the component (C) and the component (B), the average number of moles of ethylene oxide (EO) added in the polyoxyethylene hydrogenated castor oil is preferably from 15 to 80, more preferably from 20 to 60, further preferably from 25 to 50. In view of ensuring the stability of the component (A) while using the component (A) in combination with the component (C) and the component (B), the content of the component (D) is 0.4% by mass or more, preferably 0.45% by mass or more, more preferably 0.5% by mass or more, in the liquid composition for oral cavity of the present invention. On the other hand, in view of ensuring the adsorptivity of the component (A) on gingiva, the content of the component (D) is 1.1% by mass or less, preferably 1% by mass or less, in the liquid composition for oral cavity of the present invention. Moreover, the content of the component (D) is 0.4% by mass or more and 1.1% by mass or less, preferably from 0.45% to 1.1% by mass, more preferably from 0.45% to 1% by mass, in the liquid composition for oral cavity of the present invention.

In view of ensuring the stability of the component (A) while using the component (A) in combination with the component (C) and the component (B), the mass ratio between the component (D) and the component (A), ((D)/(A)), is preferably 8 or more, more preferably 10 or more. On the other hand, in view of ensuring the adsorptivity of the component (A) on gingiva, the mass ratio ((D)/(A)) is preferably 40 or less, more preferably 35 or less, further preferably 32 or less.

The liquid composition for oral cavity of the present invention comprises, as a component (E), an organic acid and a salt thereof. In view of the stability of the component (A), the organic acid and the salts thereof are preferably an organic acid having buffering capacity and salts thereof, more preferably one or more selected from the group consisting of hydroxycarboxylic acids and salts thereof, even more preferably one or more selected from the group consisting of citric acid, lactic acid, malic acid and salts thereof, further preferably one or more selected from the group consisting of citric acid, lactic acid and salts thereof. In view of the stability of the component (A), the content of the component (E) is preferably 0.02% by mass or more, more preferably 0.04% by mass or more, in the liquid composition for oral cavity of the present invention. On the other hand, in view of flavor, the content of the component (E) is preferably 0.2% by mass or less, more preferably 0.15% by mass or less, in the liquid composition for oral cavity of the present invention. It is to be noted that the organic acid salt used in the liquid composition for oral cavity of the present invention may also be an organic acid salt obtained by blending an organic acid with sodium hydroxide, or an organic acid with potassium hydroxide.

In view of the stability of the component (A), the pH at 25° C. of the liquid composition for oral cavity of the present invention is 5 or more, preferably 5.2 or more, more preferably 5.5 or more, and it is also 6.8 or less, preferably 6.5 or less. By using the above described component (E), the pH of the liquid composition for oral cavity of the present invention can be adjusted to a pH value ranging in the above described range.

The liquid composition for oral cavity of the present invention comprises, as a component (F), 70% by mass or more and 97% by mass or less of water. The water used as a component (F) in the present invention refers to the total moisture content of the liquid composition for oral cavity, and specifically the water used as a component (F) encompasses not only purified water or the like blended into the liquid composition for oral cavity, but also water contained in each component, such as a 50% sodium lactate solution (aqueous solution) used upon formulation. By containing water as a component (F), the composition can be favorably dispersed in the oral cavity. In view of ensuring the dispersibility of the liquid composition for oral cavity in the oral cavity or the feeling of use thereof, the content of the component (F) is 70% by mass or more, preferably 75% by mass or more, more preferably 80% by mass or more, in the liquid composition for oral cavity of the present invention. On the other hand, in view of keeping balance with other components, the content of the component (F) is 97% by mass or less, more preferably 96.5% by mass or less, further preferably 96.2% by mass or less, in the liquid composition for oral cavity of the present invention. Moreover, the content of the component (F) is 70% by mass or more and 97% by mass or less, preferably from 75% to 96.5% by mass, more preferably from 80% to 96.2% by mass, in the liquid composition for oral cavity of the present invention.

The liquid composition for oral cavity of the present invention can comprise an oily component (G) other than surfactants, which is a component other than the component (D) and the component (A). Examples of such a component (G) include one or more selected from the group consisting of: an oil-soluble medicinal component, such as a flavor, tocopherol, triclosan, and isopropyl methylphenol; and an oily preservative, such as sodium benzoate, ethyl p-hydroxybenzoate, propyl p-hydroxybenzoate, isobutyl p-hydroxybenzoate, isopropyl p-hydroxybenzoate, and butyl p-hydroxybenzoate.

Tocopherol is a component which has been also known as vitamin E. In view of blood circulation-promoting action and the like, preferred examples of such a component include one or more selected from the group consisting of: α-tocopherol, β-tocopherol, γ-tocopherol, and δ-tocopherol; and derivatives including tocopherol acetate such as dl-α-tocopherol acetate, tocopherol nicotinate, and tocopherol succinate. Among them, α-tocopherol and tocopherol acetate are more preferable, and dl-α-tocopherol acetate is further preferable.

Triclosan is a halogenated diphenyl ether-type bactericide having a wide range of antibacterial spectrum, and its chemical name is 2',4,4'-trichloro-2-hydroxydiphenyl ether. For instance, Triclosan is commercially available as a brand name "Irgacare MP" from Ciba Specialty Chemicals.

Isopropyl methylphenol is also a bactericide having a wide range of antibacterial spectrum, and its chemical name is 1-hydroxy-4-isopropyl-3-methylphenol. For instance, isopropyl methylphenol is commercially available as a brand name "Biosol" from Osaka Kasei Co., Ltd. It is to be noted that isopropyl methylphenol is also referred to as 3-methyl-4-isopropylphenol or cymen-5-ol.

Examples of the flavor include: a natural flavor component such as peppermint oil, spearmint oil, cinnamon oil, anise oil, Eucalyptus oil, wintergreen oil, Cassia oil, clove oil, thyme oil, sage oil, sage clary oil, nutmeg oil, funnel oil, lemon oil, orange oil, mentha oil, cardamon oil, coriander oil, basil oil, mandarin oil, lime oil, lavender oil, rosemary oil, ginger oil, grapefruit oil, laurel oil, chamomile oil, caraway oil, marjoram oil, bay oil, lemon glass oil, lemon balm oil, pimento berry oil, palmarosa oil, olibanum oil, pine needle oil, petitgrain oil, neroli oil, rose oil, and jasmine oil, and a flavor component obtained by processing the natural flavor component; a single flavor component such as menthol, pulegol carvone, anethole, cineol, methyl salicylate, cinnamic aldehyde, eugenol, 3-1-menthoxypropane-1,2-diol thymol, citronellyl acetate, linalool, linalyl acetate, geraniol, geranyl acetate, citronellol, limonene, menton, menthyl acetate, n-substituted-p-menthane-3-carboxamide, pinene, octylaldehyde, citral, pulegone, carbyl acetate, dihydrocarbyl acetate, anisaldehyde, benzaldehyde, camphor, lactone, ethyl acetate, ethyl butylate, allylcyclohexyl propionate, methyl anthranilate, ethylmethylphenyl glycidate, vanillin, undecalactone, hexanal, butyl acetate, isoamyl acetate, hexenol, dimethyl sulfide, cyclotene, furfural, trimethylpyrazine, ethyl lactate, methyl lactate, and ethyl thioacetate; and a compound flavor component such as strawberry flavor, apple flavor, banana flavor, pineapple flavor, grape flavor, mango flavor, butter flavor, milk flavor, fruit mix flavor, and tropical fruit flavor. In view of ensuring dispersibility or solubility while providing good flavor and the like, the content of the flavor is preferably 0.1% by mass or more and preferably 0.7% by mass or less, more preferably 0.5% by mass or less, in the liquid composition for oral cavity of the present invention. In the case of using such a flavor, in view of good dispersion or dissolution of such a flavor, it is preferable to use a mixture obtained by previously mixing the flavor with a very small portion of propylene glycol as a component (c), namely, with a trace amount of the component (c) which corresponds to 0.5% by mass or more and 5% by mass or less of the entire flavor.

In view of preventing the white turbidity and precipitates in the liquid composition for oral cavity, the total content of the component (G) and the component (A) is preferably 0.8% by mass or less, more preferably 0.7% by mass or less, further preferably 0.5% by mass or less, in the liquid composition for oral cavity of the present invention. In view of enhancing flavor, and in view of improving the pharmacological effects of medicinal components, the total content of the component (G) and the component (A) is preferably 0.12% by mass or more, more preferably 0.2% by mass or more, further preferably 0.3% by mass or more, in the liquid composition for oral cavity of the present invention.

In view of preventing the white turbidity of and precipitates in the liquid composition for oral cavity, the mass ratio between the content of the component (D) and the total content of the component (G) and the component (A), ((D)/((G)+(A))), is preferably 0.8 or more, more preferably 1 or more, and further preferably 1.2 or more. In view of improving adsorptivity of the component (A) and other oily active ingredients on gingiva, ((D)/((G)+(A))) is preferably 4 or less, more preferably 3.5 or less, and further preferably 3.2 or less.

In view of ensuring stability and transparent or semi-transparent appearance, the content of water-insoluble powders, such as abrasive powders or thickening silica, in the liquid composition for oral cavity of the present invention is preferably limited. The content of such water-insoluble powders is preferably 0.01% by mass or less, more preferably 0.005% by mass or less, in the liquid composition for oral cavity of the present invention, or the liquid composition for oral cavity of the present invention preferably contains no water-insoluble powders.

The liquid composition for oral cavity of the present invention can comprise polyol other than the component (C). Such polyol is preferably one or more selected from the group consisting of glycerin, sorbitol, xylitol, erythritol, 1,3-butylene glycol and polyethylene glycol, and is more preferably one or two or more selected from the group consisting of glycerin, sorbitol, and xylitol having solubility in water at 25° C. of 50% or more. In view of flavor, the total content of polyol other than the component (C) is preferably 10% by mass or less, and more preferably 7% by mass or less, in the liquid composition for oral cavity of the present invention. The liquid composition for oral cavity may contain no polyol other than the component (C), but when the liquid composition contains the polyol other than the component (C), the total content of the polyol other than the component (C) is preferably 1% by mass or more, more preferably 2% by mass or more, in the liquid composition for oral cavity of the present invention.

Moreover, among the polyols other than the component (C), the content of glycerin is further preferably 5% by mass or less, and the total content of one or more selected from the group consisting of sorbitol and xylitol is further preferably 5% by mass or less in the liquid composition for oral cavity of the present invention. Moreover, in view of preventing the white turbidity and precipitates in the liquid composition for oral cavity, among the polyols other than the component (C), the content of erythritol is further preferably 2% by mass or less in the liquid composition for oral cavity of the present invention, and the total content of one or more selected from the group consisting of 1,3-butylene glycol and polyethylene glycol, which are polyols other than the component (C), is further preferably 2% by mass or less in the liquid composition for oral cavity of the present invention.

In view of enhancing both adsorptivity of the component (A) on gingiva and stability in good, the content of surfactants other than the component (D), namely, the content of a nonionic surfactant, anionic surfactant, cationic surfactant, and amphoteric surfactant other than the component (D), in the liquid composition for oral cavity of the present invention is preferably limited. The total content of such surfactants other than the component (D) is preferably 0.2% by mass or less, more preferably 0.1% by mass or less, further preferably 0.01% by mass or less, in the liquid composition for oral cavity of the present invention. The total content of such surfactants other than the component (D) is preferably 10% by mass or less of the content of the component (D), and the present liquid composition for oral cavity preferably contains no surfactants other than the component (D).

Specifically, in view of ensuring adsorptivity of the component (A) on gingiva while comprising the component (D), the content of nonionic surfactants other than the component (D), namely, the total content of one or more nonionic surfactants selected from the group consisting of polyethylene glycol fatty acid esters such as polyethylene glycol monolaurate, polyethylene glycol monostearate and polyethylene glycol monooleate, isostearyl glyceryl ether, and a polyoxyethylene-polyoxypropylene block copolymer is preferably 0.05% by mass or less, more preferably 0.01% by mass or less, further preferably 0.001% by mass or less, in the liquid composition for oral cavity of the present invention, or the present liquid composition for oral cavity preferably contains no nonionic surfactants other than the component (D).

The liquid composition for oral cavity of the present invention may contain a water-soluble medicinal component other than the component (B). Examples of such a water-soluble medicinal component include: an anti-inflammatory agent such as allantoin (chemical name: 5-ureidohydantoin) or a salt thereof (allantoin acetyl-DL-methionine, allantoin polygalacturonic acid, allantoin ascorbic acid, allantoin glycyl, allantoin dihydroxyaluminum (aldioxa), allantoin chlorohydroxyaluminum (alcloxa), etc.), tranexamic acid, and epsilon aminocaproic acid; a cationic bactericide other than the component (B) such as chlorhexidine hydrochloride and benzethonium chloride; an amphoteric bactericide such as dodecyl diaminoethyl glycine; an agent for preventing or ameliorating hypersensitivity such as aluminum lactate, potassium nitrate, and strontium chloride; water-soluble vitamin such as vitamin C and vitamin B; a plant extract, such as *Thujopsis dolabrata* extract, phellodendron bark extract, Japanese *angelica* a root extract, *Scutellaria* root extract, chamomile extract, rhatany extract, and myrrh extract; and a polyphenol. The content of the water-soluble medicinal component is preferably 1% by mass or less, more preferably 0.7% by mass or less, further preferably 0.5% by mass or less, in the liquid composition for oral cavity of the present invention, or the present liquid composition for oral cavity may contain no water-soluble medicinal component. When the present liquid composition for oral cavity comprises such water-soluble medicinal component, the content of the water-soluble medicinal component is preferably 0.01% by mass or more, more preferably 0.1% by mass or more, in the liquid composition for oral cavity of the present invention.

In view of giving fresh feeling, the liquid composition for oral cavity of the present invention can contain ethanol. In view of giving fresh feeling, the content of the ethanol is preferably 0.01% by mass or more, more preferably 1% by mass or more, in the liquid composition for oral cavity of the present invention. On the other hand, in view of suppressing bitter taste or irritation, and in view of ensuring the adsorptivity of the component (A) on gingiva, the content of the ethanol is preferably 8% by mass or less, more preferably 6% by mass or less, further preferably 5% by mass or less, in the liquid composition for oral cavity of the present invention. Moreover, the content of the ethanol is preferably from 0.01% to 8% by mass, more preferably from 1% to 6% by mass, further preferably from 1% to 5% by mass, in the liquid composition for oral cavity of the present invention.

The liquid composition for oral cavity of the present invention can contain, as appropriate, for example, a sweetener such as saccharin sodium and aspartame, a pigment, a coloring matter and the like, as well as the aforementioned components, unless they inhibit the effects of the present invention.

The liquid composition for oral cavity of the present invention is a transparent or semi-transparent liquid composition for oral cavity, in which the component (A) can be stably dispersed or dissolved, and the present liquid composition for oral cavity may also be colored. The phrase "the liquid composition for oral cavity of the present invention is transparent or semi-transparent" is used to specifically mean that when the liquid composition for oral cavity is filled into a cell having an optical path length of 10 mm, the transmittance of light with an absorption wavelength of 550 nm is 80% or more. The transmittance is preferably 90% or more, and more preferably 95% or more. It is to be noted that the cell to be used is a quartz cell.

The liquid composition for oral cavity of the present invention is obtained by blending the component (B) and the component (A) simultaneously, or by blending the component (B) before the component (A). More specifically, the production method for obtaining the liquid composition for oral cavity of the present invention is a method comprising the following step 1 to step 4:

(Step 1) a step of blending water (F) with an organic acid and a salt thereof (E) to adjust the pH of a resultant mixture at 25° C. to 5 or more and 6.8 or less, (Step 2) a step of blending 0.01% by mass or more and 0.1% by mass or less of cetylpyridinium chloride (B) into the mixture, (Step 3) a step of blending 0.02% by mass or more and 0.1% by mass or less of β-glycyrrhetinic acid (A) and 2% by mass or more and 10% by mass or less of propylene glycol (C) into the mixture, and (Step 4) a step of blending 0.4% by mass or more and 1.1% by mass or less of polyoxyethylene hydrogenated castor oil (D) into the mixture, wherein a mass ratio between the component (A) and the component (B), ((A)/(B)), is 0.3 or more and 1.3 or less, after completion of the step 1, the step 2 and the step 3 are simultaneously carried out, or the step 2 is carried out, followed by carrying out the step 3, and the step 4 and any one of the steps 1 to 3 are simultaneously carried out, or the step 4 is carried out independently from the steps 1 to 3.

In the method for producing a liquid composition for oral cavity of the present invention, for example, the phrase "step X is carried out, followed by carrying out step Y" means that the timing of carrying out step Y may be any timing from initiation of the production to the end of the production, as long as it is carried out after step X has been carried out, and thus, the aforementioned phase is not limited only to the case where step Y is carried out immediately after step X has been carried out. Accordingly, unless otherwise specified, the phrase "step X is carried out, followed by carrying out step Y" includes a case where another step is carried out between the step X and the step Y, specifically, for example, a case where "step X is carried out, step Z is then carried out, and thereafter, step Y is carried out".

The step 1 included in the method for producing a liquid composition for oral cavity of the present invention is a step of blending water (F) with an organic acid and a salt thereof (E) to adjust the pH of the obtained mixture at 25° C. to 5 or more and 6.8 or less. The pH can be adjusted to the aforementioned range by blending the component (E). The step 1 is a first step among the steps 1 to 4 included in the method for producing a liquid composition for oral cavity of the present invention, and thus the steps following the step 1 can be carried out in an environment in which the pH has been adjusted to the specific range. In view of the stability of the component (A), the pH of the mixture at 25° C. adjusted by performing the step 1 is 5 or more, preferably 5.2 or more, more preferably 5.5 or more, and it is also 6.8 or less, and preferably 6.5 or less.

With regard to the step 2 and the step 3 included in the method for producing a liquid composition for oral cavity of the present invention, after completion of the step 1, the step 2 and the step 3 are simultaneously carried out, or the step 2 is carried out, followed by carrying out the step 3. The phrase "after completion of the step 1, the step 2 and the step 3 are simultaneously carried out" means that, after completion of the step 1, the component (B) to be blended in the step (2) and the component (A) and the component (C) to be blended in the step (3) are simultaneously blended, or that the components (A) to (C) are mixed with one another at once to obtain a mixed solution, followed by blending the mixed solution into the aqueous solution, which is the mixture of the component (F) and the component (E), has a pH value of 5 or more and 6.8 or less, and has been obtained in the step 1.

When the component (G), which is an oily component such as a flavor, is blended, it is preferable that the component (G) be blended into the mixture simultaneously with the component (D) in the step 4, or that the component (D) be mixed with the component (G), followed by blending the obtained mixed solution as a component containing the component (G) in the subsequent step. Moreover, in the case of using a flavor among the components (G), it is preferable to use a flavor which has previously been mixed with a very small portion of propylene glycol used as a component (C) (component (C-2)), and in this case, the balance of component (C) (component (C-1)) excluding the component (C-2) which has been mixed with the flavor is blended into the mixture in the step 3. The propylene glycol (component (C-2)) used in this case is in a trace amount, as described above. Hence, although the amount of the propylene glycol as the component (C-1) in the step 3 is an amount obtained by subtracting the amount used as the component (C-2) from the total amount of the component (C), there is no difference in the above described amount of the component (C).

More specifically, in the case of using a flavor which has been mixed with a very small portion of propylene glycol used as a component (C) (component (C-2)), the content of the component (C-2) is preferably 0.035% by mass or less, more preferably 0.025% by mass or less, and it is also preferably 0.01% by mass or more, in the liquid composition for oral cavity of the present invention. It may be adequate that the amount of the component (C-1) may be an amount obtained by subtracting the amount of the component (C-2) from the above-described amount of the component (C) in the step 3. Moreover, the amount of the component (C) in the step 3, in which 0.02% by mass or more and 0.1% by mass or less of β-glycyrrhetinic acid (A) and 2% by mass or more and 10% by mass or less of propylene glycol (C) are blended into the mixture, may be either the total amount of the component (C) in the liquid composition for oral cavity, or the amount of the component (C-1) obtained by subtracting therefrom the amount of the component (C-2) to be mixed with a flavor.

Furthermore, in a case where a water-soluble component including polyols other than the component (C), such as glycerin or sorbitol, or a sweetener such as saccharin sodium or aspartame; or a water-soluble medicinal component is blended, these components may be blended at any timing, and the components can also be blended in a final step after completion of all steps including the steps 1 to 4.

The step 4 included in the method for producing a liquid composition for oral cavity of the present invention is a step which is carried out simultaneously with any one of the steps 1 to 3, or a step which is carried out independently from the steps 1 to 3. That is to say, the step 4 may be carried out simultaneously with any one of the steps 1 to 3, or may also be carried out before or after the steps 1 to 3 are carried out. In view of productivity, it is preferable that the step 4 be carried out simultaneously with the step 2, or that the step 4 be carried out after the step 2 has been carried out. Further, in view of productivity, the step 3 is preferably carried out, independently, as a step different from the step 4.

With regard to the above described steps 1 to 4 included in the method for producing a liquid composition for oral cavity of the present invention, the mass ratio between the component (A) and the component (B), ((A)/(B)), is 0.3 or more and 1.3 or less. In addition, in view of preventing degradation of oily components such as the component (A) and the component (G), etc., all of these steps 1 to 4 are preferably carried out at a temperature of 15° C. or higher and 35° C. or lower. The preferred amounts and mass ratios of individual components used in the steps 1 to 4 are preferably the same as the aforementioned preferred contents and mass ratios of individual components.

The liquid composition for oral cavity of the present invention can be preferably used as a mouth wash, a liquid toothpaste, or a mouth wash liquid.

With regard to the aforementioned embodiments of the present invention, the following method for producing a liquid composition for oral cavity and the following liquid composition for oral cavity will be further disclosed.

[1] A method for producing a liquid composition for oral cavity, comprising the following step 1 to step 4:

(Step 1) a step of blending water (F) with an organic acid and a salt thereof (E) to adjust the pH of a resultant mixture at 25° C. to 5 or more and 6.8 or less, (Step 2) a step of blending 0.01% by mass or more and 0.1% by mass or less of cetylpyridinium chloride (B) into the mixture, (Step 3) a step of blending 0.02% by mass or more and 0.1% by mass or less of β-glycyrrhetinic acid (A) and 2% by mass or more and 10% by mass or less of propylene glycol (C) into the mixture, and (Step 4) a step of blending 0.4% by mass or more and 1.1% by mass or less of polyoxyethylene hydrogenated castor oil (D) into the mixture, wherein a mass ratio between the component (A) and the component (B), ((A)/(B)), is 0.3 or more and 1.3 or less, after completion of the step 1, the step 2 and the step 3 are simultaneously carried out, or the step 2 is carried out, followed by carrying out the step 3, and the step 4 and any one of the steps 1 to 3 are simultaneously carried out, or the step 4 is carried out independently from the steps 1 to 3.

[2] The method for producing a liquid composition for oral cavity according to the above [1], wherein the pH of the mixture at 25° C. adjusted in the step 1 is preferably 5.2 or more, more preferably 5.5 or more, and it is 6.8 or less, preferably 6.5 or less.

[3] The method for producing a liquid composition for oral cavity according to the above [1] or [2], wherein the method comprises blending into the mixture an oily component (G) other than surfactants, which is a component other than the component (D) and the component (A), wherein, the component (G) and the component (D) are simultaneously blended into the mixture in the step 4, or the component (D) is mixed with the component (G) to obtain a mixed solution, followed by blending the mixed solution as a component comprising the component (G) into the mixture in the subsequent step.

[4] The method for producing a liquid composition for oral cavity according to any one of the above [1] to [3], wherein the method comprises blending a flavor into the mixture, wherein a mix is previously prepared by mixing the flavor with a very small portion of propylene glycol used as the component (C) (component (C-2)), followed by blending the mix thus obtained into the mixture, and in the step 3, the balance of the component (C) (component (C-1)), which excludes the component (C-2) mixed with the flavor, is blended into the mixture in the step 3. [5] The method for producing a liquid composition for oral cavity according to any one of the above [1] to [4], wherein preferably, the step 4 is carried out simultaneously with the steps 1 to 3, or is carried out before or after the steps 1 to 3, more preferably, the step 4 is carried out simultaneously with the step 2, or is carried out after the step 2.

[6] The method for producing a liquid composition for oral cavity according to any one of the above [1] to [5], wherein the step 3 and the step 4 are independently carried out.

[7] The method for producing a liquid composition for oral cavity according to any one of the above [1] to [6], wherein the steps 1 to 4 are carried out at a temperature of 15° C. or higher and 35° C. or lower.

[8] The method for producing a liquid composition for oral cavity according to any one of the above [1] to [7], wherein the amount of the component (F) is 70% by mass or more and 97% by mass or less in the liquid composition for oral cavity.

[9] A method for producing a liquid composition for oral cavity, which comprises blending the following components (A) to (F)

(A) 0.02% by mass or more and 0.1% by mass or less of β-glycyrrhetinic acid, (B) 0.01% by mass or more and 0.1% by mass or less of cetylpyridinium chloride, (C) 2% by mass or more and 10% by mass or less of propylene glycol, (D) 0.4% by mass or more and 1.1% by mass or less of polyoxyethylene hydrogenated castor oil, (E) an organic acid and a salt thereof, and (F) 70% by mass or more and 97% by mass or less of water, wherein
the composition having a pH at 25° C. of 5 or more and 6.8 or less, and a mass ratio between the component (A) and the component (B), ((A)/(B)), of 0.3 or more and 1.3 or less,
wherein the component (B) and the component (A) are simultaneously blended, or the component (B) is blended before the component (A) is blended.

[10] The method for producing a liquid composition for oral cavity according to any one of the above [1] to [9], wherein the amount of the component (A) is 0.02% by mass or more, preferably 0.025% by mass or more, and it is 0.1% by mass or less, preferably 0.08% by mass or less, further preferably 0.05% by mass or less, in the liquid composition for oral cavity of the present invention.

[11] The method for producing a liquid composition for oral cavity according to any one of the above [1] to [10], wherein the amount of the component (B) is 0.01% by mass or more, preferably 0.02% by mass or more, more preferably 0.03% by mass or more, and it is 0.1% by mass or less, preferably 0.08% by mass or less, more preferably 0.07% by mass or less, in the liquid composition for oral cavity of the present invention.

[12] The method for producing a liquid composition for oral cavity according to any one of the above [1] to [11], wherein the amount of the component (F) is 70% by mass or more, preferably 75% by mass or more, more preferably 80% by mass or more, and it is 97% by mass or less, more preferably 96.5% by mass or less, further preferably 96.2% by mass or less, in the liquid composition for oral cavity of the present invention.

[13] The method for producing a liquid composition for oral cavity according to any one of the above [1] to [12], wherein a mass ratio between the component (D) and the component (A), ((D)/(A)), is preferably 8 or more, more preferably 10 or more, and it is preferably 40 or less, more preferably 35 or less, further preferably 32 or less.

[14] The method for producing a liquid composition for oral cavity according to any one of the above [1] to [13], wherein the method comprises blending into the mixture an oily component (G) other than surfactants, which is a component other than the component (D) and the component (A), wherein a mass ratio between the amount of the component (D) and the total amount of the component (G) and the component (A), ((D)/((G)+(A))), is preferably 0.8 or more, more preferably 1 or more, further preferably 1.2 or more, and it is preferably 4 or less, more preferably 3.5 or less, further preferably 3.2 or less.

[15] The method for producing a liquid composition for oral cavity according to any one of the above [1] to [14], wherein a mass ratio between the amount of the component (C) and the amount of the component (A), ((C)/(A)), is preferably 40 or more, more preferably 50 or more, further preferably 60 or more, and it is preferably 500 or less, more preferably 300 or less, further preferably 250 or less.

[16] The method for producing a liquid composition for oral cavity according to any one of the above [1] to [15], wherein the mass ratio between the amount of the component (A) and the amount of the component (B), ((A)/(B)), is preferably 1.1 or less, more preferably 1 or less, and it is preferably 0.4 or more.

[17] The method for producing a liquid composition for oral cavity according to any one of the above [1] to [16], wherein the amount of the component (C) is 2% by mass or more and 10% by mass or less, preferably from 3% to by mass, in the liquid composition for oral cavity of the present invention.

[18] The method for producing a liquid composition for oral cavity according to any one of the above [1] to [17], wherein the amount of the component (D) is 0.4% by mass or more, preferably 0.45% by mass or more, more preferably 0.5% by mass or more, and it is 1.1% by mass or less, preferably 1% by mass or less, in the liquid composition for oral cavity of the present invention.

[19] The method for producing a liquid composition for oral cavity according to any one of the above [1] to [18], wherein the amount of the component (E) is preferably 0.02% by mass or more, more preferably 0.04% by mass or more, and it is preferably 0.2% by mass or less, more preferably 0.15% by mass or less, in the liquid composition for oral cavity of the present invention.

[20] The method for producing a liquid composition for oral cavity according to any one of the above [9] to [19], wherein the pH at 25° C. is adjusted to be 5 or more, preferably 5.2 or more, more preferably 5.5 or more, and it is adjusted to be 6.8 or less, preferably 6.5 or less.

[21] The method for producing a liquid composition for oral cavity according to any one of the above [1] to [20], wherein the method comprises blending a flavor into the mixture, wherein the amount of the flavor is preferably 0.1% by mass or more, and it is preferably 0.7% by mass or less, more preferably 0.5% by mass or less, in the liquid composition for oral cavity of the present invention.

[22] The method for producing a liquid composition for oral cavity according to any one of the above [1] to [21], wherein the amount of surfactants other than the component (D) is preferably 0.2% by mass or less, more preferably 0.1% by mass or less, further preferably 0.01% by mass or less in the liquid composition for oral cavity of the present invention, and it is preferably 10% by mass or less of the content of the component (D), or such surfactants other than the component (D) are not blended.

[23] The method for producing a liquid composition for oral cavity according to any one of the above [1] to [22], wherein the amount of nonionic surfactants other than the component (D) is preferably 0.05% by mass or less, more preferably 0.01% by mass or less, further preferably 0.001% by mass or less in the liquid composition for oral cavity of the present invention, or nonionic surfactants other than the component (D) are not blended.

[24] The method for producing a liquid composition for oral cavity according to any one of the above [1] to [23], wherein the amount of glycerin is further preferably 5% by mass or less in the liquid composition for oral cavity of the present invention, the total amount of one or more selected from the group consisting of sorbitol and xylitol is further preferably 5% by mass or less in the liquid composition for oral cavity of the present invention, the amount of erythritol is further preferably 2% by mass or less in the liquid composition for oral cavity of the present invention, or the total amount of one or more selected from the group consisting of 1,3-butylene glycol and polyethylene glycol is further preferably 2% by mass or less in the liquid composition for oral cavity of the present invention.

[25] A liquid composition for oral cavity, comprising the following components (A) to (F):
(A) 0.02% by mass or more and 0.1% by mass or less of β-glycyrrhetinic acid,
(B) 0.01% by mass or more and 0.1% by mass or less of cetylpyridinium chloride,
(C) 2% by mass or more and 10% by mass or less of propylene glycol,
(D) 0.4% by mass or more and 1.1% by mass or less of polyoxyethylene hydrogenated castor oil, (E) an organic acid and a salt thereof, and
(F) 70% by mass or more and 97% by mass or less of water, wherein
the pH of the liquid composition at 25° C. is 5 or more and 6.8 or less, a mass ratio between the component (A) and the component (B), ((A)/(B)), is 0.3 or more and 1.3 or less, and the liquid composition is transparent or semi-transparent.

[26] The liquid composition for oral cavity according to the above [25], wherein the content of the component (A) is preferably 0.025% by mass or more, and it is 0.1% by mass or less, preferably 0.08% by mass or less, further preferably 0.05% by mass or less.

[27] The liquid composition for oral cavity according to the above [25] or [26], wherein the content of the component (B) is preferably 0.02% by mass or more, more preferably 0.03% by mass or more, and it is 0.1% by mass or less, preferably 0.08% by mass or less, more preferably 0.07% by mass or less.

[28] The liquid composition for oral cavity according to any one of the above [25] to [27], wherein the content of the component (F) is preferably 75% by mass or more, more preferably 80% by mass or more, and it is 97% by mass or less, more preferably 96.5% by mass or less, further preferably 96.2% by mass or less.

[29] The liquid composition for oral cavity according to any one of the above [25] to [28], wherein a mass ratio between the component (D) and the component (A), ((D)/(A)), is preferably 8 or more, more preferably 10 or more, and it is preferably 40 or less, more preferably 35 or less, further preferably 32 or less.

[30] The liquid composition for oral cavity according to any one of the above [25] to [29], wherein the liquid composition comprises an oily component (G) other than surfactants, which is a component other than the component (D) and the component (A), wherein a mass ratio between the content of the component (D) and the total content of the component (G) and the component (A), ((D)/((G)+(A))), is preferably 0.8 or more, more preferably 1 or more, further preferably 1.2 or more, and it is preferably 4 or less, more preferably 3.5 or less, further preferably 3.2 or less.

[31] The liquid composition for oral cavity according to any one of the above [25] to [30], wherein a mass ratio between the content of the component (C) and the content of the component (A), ((C)/(A)), is preferably 40 or more, more preferably 50 or more, further preferably 60 or more, and it is preferably 500 or less, more preferably 300 or less, further preferably 250 or less.

[32] The liquid composition for oral cavity according to any one of the above [25] to [31], wherein the mass ratio of the content of the component (A) and the content of the component (B), ((A)/(B)), is preferably 1.1 or less, more preferably 1 or less, and it is preferably 0.4 or more.

[33] The liquid composition for oral cavity according to any one of the above [25] to [32], wherein the content of the component (C) is preferably from 3% to 8% by mass.

[34] The liquid composition for oral cavity according to any one of the above [25] to [33], wherein the content of the component (D) is preferably 0.45% by mass or more, more preferably 0.5% by mass or more, and it is preferably 1% by mass or less.

[35] The liquid composition for oral cavity according to any one of the above [25] to [34], wherein the content of the component (E) is preferably 0.02% by mass or more, more preferably 0.04% by mass or more, and it is preferably 0.2% by mass or less, more preferably 0.15% by mass or less.

[36] The liquid composition for oral cavity according to any one of the above [25] to [35], wherein the pH at 25° C. is 5 or more, preferably 5.2 or more, more preferably 5.5 or more, and it is 6.8 or less, preferably 6.5 or less.

[37] The liquid composition for oral cavity according to any one of the above [25] to [36], wherein the composition comprises a flavor, wherein the content of the flavor is preferably 0.1% by mass or more, and it is preferably 0.7% by mass or less, more preferably 0.5% by mass or less.

[38] The liquid composition for oral cavity according to any one of the above [25] to [37], wherein the content of surfactants other than the component (D) is preferably 0.2% by mass or less, more preferably 0.1% by mass or less, further preferably 0.01% by mass or less, and it is preferably 10% by mass or less of the content of the component (D), or such surfactants other than the component (D) are not contained.

[39] The liquid composition for oral cavity according to any one of the above [25] to [38], wherein the content of nonionic surfactants other than the component (D) is preferably 0.05% by mass or less, more preferably 0.01% by mass or less, further preferably 0.001% by mass or less, or such nonionic surfactants other than the component (D) are not contained.

[40] The liquid composition for oral cavity according to any one of the above [25] to [39], wherein the content of glycerin is further preferably 5% by mass or less, the total content of one or more selected from the group consisting of sorbitol and xylitol is further preferably 5% by mass or less, the content of erythritol is further preferably 2% by mass or less, or the total content of one or more selected from the group consisting of 1,3-butylene glycol and polyethylene glycol is further preferably 2% by mass or less.

[41] Use of the liquid composition for oral cavity according to any one of the above [25] to [39] for increasing the amount of β-glycyrrhetinic acid adsorbed on gingiva.

[42] Use of the liquid composition for oral cavity according to any one of the above [25] to [39] for washing mouth.

EXAMPLES

Hereinafter, the present invention will be specifically described based on the following examples. It is to be noted that the content of each component is indicated with % by mass, unless otherwise specified in the following tables.

Examples 1 to 4 and Comparative Example 1

According to the composition shown in Table 1, each mouth wash liquid was prepared at a room temperature (25° C.) according to the following production method.

First, organic acid or salts thereof (E) had previously was blended into purified water (F) to obtain an aqueous solution having a pH of 6. Thereafter, cetylpyridinium chloride (B) was blended into the aqueous solution, followed by mixing, and a mixed solution of polyoxyethylene hydrogenated castor oil (D) and an oily component (G) such as a flavor was further blended into the mixture. Subsequently, a mixed solution of a component (A) and a component (C) was blended into the mixture, and finally, a water-soluble component such as glycerin or sorbitol was blended into the mixture, followed by mixing.

Thereafter, using the obtained mouth wash liquid, the amount of β-glycyrrhetinic acid adsorbed was measured according to the below-mentioned method.

<<Measurement of the Amount of β-Glycyrrhetinic Acid Adsorbed>>

0.1 g of Keratin powders (mean particle diameter: 8 μm, protein content: 95% by weight) was added to 6 mL of the mouse wash liquid immediately after the preparation thereof. The mixed solution was shaken for 5 minutes, using a Vortex mixer (SHIBATA TEST TUBE MIXER TTM-1, manufactured by SHIBATA SCIENTIFIC TECHNOLOGY LTD.), and was then left to stand still at a room temperature (25° C.) for 1 hour. Thereafter, the resulting solution was subjected to centrifugation (2,000 rpm, 10 minutes), and a supernatant was then recovered. Thereafter, 6 mL of purified water was further added to the remaining keratin powders, the mixed solution was then shaken with the Vortex mixer for 5 minutes, the resulting solution was then subjected to centrifugation (2,000 rpm, 10 minutes), and a supernatant was then recovered. Keratin powders after the recovery of the supernatant were mixed with methanol, and the obtained mixture was then stirred for several minutes. Subsequently, the mixture of the keratin powders and the methanol was filtrated, and the amount of β-glycyrrhetinic acid in a filtrate, from which the keratin powders had been removed, was measured by HPLC (high performance liquid chromatography) under the following conditions.

The measured amount of β-glycyrrhetinic acid was converted to the amount of β-glycyrrhetinic acid contained in 1 g of keratin powders, and the thus obtained value is shown in Table 1.

water=8:2)) to 0.1 g of β-glycyrrhetinic acid to obtain 100 mL of a mixed solution, and then 200-fold (by volume) diluting the mixed solution with the mobile phase was used. The content of β-glycyrrhetinic acid was obtained as the product $((Z)\times(X)/(Y))$ by using a ratio between the peak area of the absorbance of β-glycyrrhetinic acid (X) and the peak area of the standard solution (Y), (X/Y), which had been measured by HPLC, and the concentration of β-glycyrrhetinic in the standard solution (Z).

Moreover, when the amount of β-glycyrrhetinic acid in Example 1 was taken as 100%, the amounts of β-glycyrrhetinic acid in Examples 2 to 4 and Comparative Example 1 are shown in Table 1.

(Measurement Conditions of HPLC)

Apparatus: Hitachi high performance liquid chromatogram La chrom Elite

Column: LiChroCART 125-4.0 LiChrospher 100 RP-18 (e) (5 μm) (Kanto Chemical Co., Inc.)

Column temperature: 40° C.

Mobile phase: 0.1 w/v % phosphoric acid-containing methanol (methanol:water=8:2)

Flow rate: 1.0 mL/min

Amount of sample injected: 20 μL

Measurement wavelength: 250 nm

TABLE 1

| | Component (% by mass) | Example 1 | Example 2 | Example 3 | Example 4 | Comparative Example 1 |
|---|---|---|---|---|---|---|
| (A) | β-Glycyrrhetinic acid | 0.03 | 0.03 | 0.03 | 0.03 | 0.03 |
| (B) | Cetylpyridinium chloride | 0.05 | 0.05 | 0.05 | 0.05 | 0.05 |
| (C) | Propylene glycol | 3 | 3 | 3 | 3 | 3 |
| (D) | Polyoxyethylene hydrogenated castor oil (40EO) *[1] | 0.5 | 0.7 | 0.9 | 1 | 1.3 |
| (G) | dl-α-Tocopherol acetate | 0.1 | 0.1 | 0.1 | 0.1 | 0.1 |
| | Flavor *[2] | 0.2 | 0.2 | 0.2 | 0.2 | 0.2 |
| | Sorbitol solution (70%) | 5 | 5 | 5 | 5 | 5 |
| | Glycerin | 3 | 3 | 3 | 3 | 3 |
| | Saccharin sodium | 0.04 | 0.04 | 0.04 | 0.04 | 0.04 |
| (E) | Lactic acid (90%) *[3] | 0.03 | 0.03 | 0.03 | 0.03 | 0.03 |
| | Sodium lactate aqueous solution (50%) | 0.2 | 0.2 | 0.2 | 0.2 | 0.2 |
| | Ethanol (95%) | 4 | 4 | 4 | 4 | 4 |
| (F) | Purified water | Balance | Balance | Balance | Balance | Balance |
| | Total | 100 | 100 | 100 | 100 | 100 |
| (F) | Total amount of water | 85.7 | 85.5 | 85.3 | 85.2 | 84.9 |
| (C) | Total amount of propylene glycol | 3.00 | 3.00 | 3.00 | 3.00 | 3.00 |
| | (A)/(B) | 0.60 | 0.60 | 0.60 | 0.60 | 0.60 |
| | (D)/(A) | 16.7 | 23.3 | 30.0 | 33.3 | 43.3 |
| | Evaluation | | | | | |
| | Amount adsorbed immediately after preparation (nmol/1 g of keratin) *[X] | 100% | 87% | 70% | 62% | 38% |

*[X] The amount of component A adsorbed, when the amount in Example 1 is set at 100%
*[1] EMANON CH-40, manufactured by Kao Corporation
*[2] Flavor shown in Table 8
*[3] Musashino Lactic Acid 90, manufactured by Musashino Chemical Laboratory Co., Ltd.

Herein, after the mouth wash liquid was applied to the keratin powders, a step of washing the mixture with purified water was performed, as described above. This is because, taking into consideration an actual situation, the situation is allowed to be similar to the state of a mouth wash liquid in the oral cavity after the mouth wash liquid has been applied into the oral cavity. In addition, the amount of β-glycyrrhetinic acid contained in the keratin powders was used as an index for the amount of β-glycyrrhetinic acid adsorbed on mucosa in the oral cavity.

It is to be noted that, as a standard solution of glycyrrhetinic acid, a solution prepared by adding a mobile phase (0.1 w/v % phosphoric acid-containing methanol (methanol:

As shown in Table 1, although the content of β-glycyrrhetinic acid as a component (A) was 0.03% by mass in each Example, when compared with the mouth wash liquid of Comparative Example 1, in which the content of polyoxyethylene hydrogenated castor oil as the component (D) which is a nonionic surfactant was more than 1.1% by mass, it was found that the mouth wash liquids of Examples 1 to 4 even having a decreased content of the component (D) each provided an extremely large amount of β-glycyrrhetinic acid adsorbed on keratin powders.

Examples 5 to 7 and Comparative Example 2

On the basis of the composition shown in Table 2, each mouth wash liquid was produced by the same production method as in Example 1. After completion of the production, the mouth wash liquid was left to stand at a room temperature (25° C.) for 1 day, and the appearance of each mouth wash liquid was then observed by naked eyes. The appearance was evaluated according to the following criteria.

The evaluation results are shown in Table 2.

<<Evaluation of Appearance>>

A: Transparent (generation of precipitates or turbidity is not observed by naked eyes).

B: There are small amounts of precipitates, or a small amount of oil is floating.

C: White turbidity is found, or many precipitates are observed.

TABLE 2

| Component (% by mass) | Example 5 | Example 6 | Example 7 | Comparative Example 2 |
|---|---|---|---|---|
| (A) β-Glycyrrhetinic acid | 0.01 | 0.03 | 0.03 | 0.05 |
| (B) Cetylpyridinium chloride | 0.03 | 0.07 | 0.07 | 0.035 |
| (C) Propylene glycol | 2 | 5 | 5 | 7 |
| (D) Polyoxyethylene hydrogenated castor oil (40EO) *1 | 0.45 | 0.9 | 0.9 | 1 |
| (G) dl-α-Tocopherol acetate | 0.05 | 0.05 | 0.1 | 0.05 |
| Flavor *2 | 0.1 | 0.1 | 0.3 | 0.1 |
| Sorbitol solution (70%) | 10 | 10 | 10 | 10 |
| Glycerin | 5 | 5 | 5 | 5 |
| (E) Lactic acid (90%) *3 | 0.03 | 0.03 | 0.03 | 0.03 |
| Sodium lactate aqueous solution (50%) | 0.2 | 0.2 | 0.2 | 0.2 |
| Ethanol (95%) | 4 | 4 | 4 | 4 |
| (F) Purified water | Balance | Balance | Balance | Balance |
| Total | 100 | 100 | 100 | 100 |
| (F) Total amount of water | 81.4 | 77.9 | 77.7 | 75.8 |
| (C) Total amount of propylene glycol | 3.00 | 5.00 | 5.00 | 5.00 |
| (A)/(B) | 0.33 | 0.43 | 0.43 | 1.43 |
| (D)/(A) | 45.0 | 30.0 | 30.0 | 20.0 |
| Evaluation | | | | |
| Evaluation of appearance | A | A | A | C |

*1 to 3 The same as those shown in Table 1

As shown in Table 2, when compared with the mouth wash liquid of Comparative Example 2, in which the mass ratio between the component (A) and the component (B) was out of the above described range, the mouth wash liquids of Examples 5 to 7, in which the contents of the components (A) to (F) were within the above described ranges and the mass ratio between the component (A) and the component (B) were within the above described range, were found to have high transparency (transparency or semi-transparency).

Examples 8 to 12 and Comparative Examples 3 to 6

According to Formulation 1 shown in Table 3, each mouth wash liquid was produced by each of the following production methods. After completion of the production, the mouth wash liquid was left to stand at a room temperature (25° C.) for 1 day, and the appearance of each mouth wash liquid was then observed by naked eyes. The appearance was evaluated according to the above described criteria.

The evaluation results are shown in Table 4.

<<Production Method>>

Details of Step 1 to Step 4

Step 1: A citric acid buffer as the component (G) was dissolved in purified water, so that the pH of the resultant solution was adjusted to be 6.

Step 2: Cetylpyridinium chloride as a component (B) was added to and mixed with the solution.

Step 3: A mixed solution of β-glycyrrhetinic acid as the component (A) and propylene glycol as the component (C) was added to and mixed with the solution.

Step 4: Polyoxyethylene hydrogenated castor oil as the component (D) was added to and mixed with the solution.

An oily component as a component (G) was mixed with the component (D) and the mixture was then added to the solution in the step 4. Water-soluble components such as sorbitol solution, glycerin, ethanol and saccharin sodium might be added in the step 1, but the water-soluble components were added and mixed with the solution in the final step in Examples 8 to 12 and Comparative Examples 3 to 6.

The order of carrying out the step 1 to the step 4

Example 8

After completion of the step 1, the step 2, the step 3 and the step 4 were carried out in this order.

Example 9

After completion of the step 1, the step 2 and the step 3 were simultaneously carried out (wherein a mixture of the components (A) to (C) was added and mixed with the solution), and thereafter, the step 4 was carried out.

Example 10

The step 1, the step 2, the step 4, and the step 3 were carried out in this order.

Example 11

After completion of the step 1, the step 2 and the step 4 were simultaneously carried out (wherein a mixture of the component (B), the component (D) and the component (G) was added and mixed with the solution), and thereafter, the step 3 was carried out.

Example 12

After completion of the step 1, the step 4 was carried out, and then, the step 2 and the step 3 were simultaneously carried out.

Comparative Example 3

After completion of the step 1, the step 3, the step 2 and the step 4 were carried out in this order.

Comparative Example 4

After completion of the step 1, the step 3, the step 2 and the step 4 were simultaneously carried out.

Comparative Example 5

After completion of the step 1, the step 3, the step 4 and the step 2 were carried out in this order.

Comparative Example 6

After completion of the step 1, the step 4, the step 3 and the step 2 were carried out in this order.

TABLE 3

| | Component (% by mass) | Formulation 1 |
|---|---|---|
| (A) | β-Glycyrrhetinic acid | 0.03 |
| (B) | Cetylpyridinium chloride | 0.05 |
| (C) | Propylene glycol | 3 |
| (D) | Polyoxyethylene hydrogenated castor oil (40EO) *1 | 0.5 |
| (G) | dl-α-Tocopherol acetate | 0.1 |
| | Flavor *2 | 0.2 |
| | Sorbitol solution (70%) | 5 |
| | Glycerin | 3 |
| | Saccharin sodium | 0.04 |
| (E) | Citric acid | 0.008 |
| | Sodium citrate | 0.042 |
| | Ethanol (95%) | 4 |
| (F) | Purified water | Balance |
| | Total | 100 |
| (F) | Total amount of water | 85.8 |
| (C) | Total amount of propylene glycol | 3.00 |
| | (A)/(B) | 0.60 |
| | (D)/(A) | 16.7 |

*1 and *2 The same as those shown in Table 1

TABLE 4

| | Example 8 | Example 9 | Example 10 | Example 11 | Example 12 | Comparative Example 3 | Comparative Example 4 | Comparative Example 5 | Comparative Example 6 |
|---|---|---|---|---|---|---|---|---|---|
| Evaluation of appearance | A | A | A | A | A | B | B | C | C |

As shown in Table 4, the mouth wash liquids of Examples 8 to 12 obtained by the production method of the present invention were found to have stable transparency, when compared with the mouth wash liquids of Comparative Examples 3 to 6.

Examples 13 to 32 and Comparative Examples 7 to 11

On the basis of the composition shown in Tables 5 to 7, each mouth wash liquid was produced according to the same production method as of Example 9. Thereafter, the appearance of the mouth wash liquid was evaluated according to the above described method, and further, the flavor of the mouth wash liquid upon the actual use thereof was evaluated according to the following method and evaluation items. The evaluation results are shown in Tables 5 to 7.

<<Evaluation of Flavor of Mouth Wash Liquid Upon Use>>

Two professional panelists put 10 mL of each mouth wash liquid into their mouth, then rinsed the mouth for 20 seconds, and then removed it from the mouth. The flavor of each mouth wash liquid during the aforementioned movements was evaluated according to the following criteria, and the results obtained by the discussion of the two panelists were used as an index for the evaluation of the flavor.

A: Good
B: It has a slightly oily flavor, or slightly soft sweetness.
C: It has an oily flavor, or soft sweetness and a bitter aftertaste.

TABLE 5

| Component (% by mass) | Example 13 | Example 14 | Example 15 | Example 16 | Example 17 | Example 18 | Example 19 | Example 20 | Example 21 |
|---|---|---|---|---|---|---|---|---|---|
| (A) β-Glycyrrhetinic acid | 0.03 | 0.03 | 0.03 | 0.03 | 0.03 | 0.03 | 0.03 | 0.03 | 0.03 |
| (B) Cetylpyridinium chloride | 0.05 | 0.05 | 0.05 | 0.05 | 0.05 | 0.05 | 0.05 | 0.05 | 0.05 |

TABLE 5-continued

| | Component (% by mass) | | | | | | | | | |
|---|---|---|---|---|---|---|---|---|---|---|
| (C) | Propylene glycol | 3 | 3 | 3 | 5 | 5 | 5 | 7 | 7 | 7 |
| (D) | Polyoxyethylene hydrogenated castor oil (40EO) *1 | 0.5 | 0.7 | 1 | 0.5 | 0.7 | 1 | 0.5 | 0.7 | 1 |
| (G) | dl-α-Tocopherol acetate | 0.1 | 0.1 | 0.1 | 0.1 | 0.1 | 0.1 | 0.1 | 0.1 | 0.1 |
| | Flavor *2 | 0.2 | 0.2 | 0.2 | 0.2 | 0.2 | 0.2 | 0.2 | 0.2 | 0.2 |
| | Glycerin | 0 | 0 | 0 | 0 | 0 | 0 | 0 | 0 | 0 |
| (E) | Citric acid | 0.008 | 0.008 | 0.008 | 0.008 | 0.008 | 0.008 | 0.008 | 0.008 | 0.008 |
| | Sodium citrate | 0.042 | 0.042 | 0.042 | 0.042 | 0.042 | 0.042 | 0.042 | 0.042 | 0.042 |
| | Total | 100 | 100 | 100 | 100 | 100 | 100 | 100 | 100 | 100 |
| (F) | Total amount of water | 96.07 | 95.87 | 95.57 | 94.07 | 93.87 | 93.57 | 92.07 | 91.87 | 91.57 |
| (C) | Total amount of propylene glycol | 3.00 | 3.00 | 3.00 | 5.00 | 5.00 | 5.00 | 7.00 | 7.00 | 7.00 |
| | (A)/(B) | 0.60 | 0.60 | 0.60 | 0.60 | 0.60 | 0.60 | 0.60 | 0.60 | 0.60 |
| | (D)/(A) | 16.7 | 23.3 | 33.3 | 16.7 | 23.3 | 33.3 | 16.7 | 23.3 | 33.3 |
| | (D)/((A) + (G)) | 1.5 | 2.1 | 3.0 | 1.5 | 2.1 | 3.0 | 1.5 | 2.1 | 3.0 |
| | (C)/(A) | 100 | 100 | 100 | 167 | 167 | 167 | 233 | 233 | 233 |
| | Evaluation of appearance | A | A | A | A | A | A | A | A | A |
| | Evaluation of flavor | A | A | A | A | A | A | A | A | A |

| | Component (% by mass) | Example 22 | Example 23 | Example 24 | Example 25 | Example 26 | Example 27 | Example 28 | Example 29 | Example 30 |
|---|---|---|---|---|---|---|---|---|---|---|
| (A) | β-Glycyrrhetinic acid | 0.05 | 0.05 | 0.05 | 0.05 | 0.05 | 0.05 | 0.05 | 0.05 | 0.05 |
| (B) | Cetylpyridinium chloride | 0.05 | 0.05 | 0.05 | 0.05 | 0.05 | 0.05 | 0.05 | 0.05 | 0.05 |
| (C) | Propylene glycol | 3 | 3 | 3 | 5 | 5 | 5 | 7 | 7 | 7 |
| (D) | Polyoxyethylene hydrogenated castor oil (40EO) *1 | 0.5 | 0.7 | 1 | 0.5 | 0.7 | 1 | 0.5 | 0.7 | 1 |
| (G) | dl-α-Tocopherol acetate | 0.1 | 0.1 | 0.1 | 0.1 | 0.1 | 0.1 | 0.1 | 0.1 | 0.1 |
| | Flavor *2 | 0.2 | 0.2 | 0.2 | 0.2 | 0.2 | 0.2 | 0.2 | 0.2 | 0.2 |
| | Glycerin | 0 | 0 | 0 | 0 | 0 | 0 | 0 | 0 | 0 |
| (E) | Citric acid | 0.008 | 0.008 | 0.008 | 0.008 | 0.008 | 0.008 | 0.008 | 0.008 | 0.008 |
| | Sodium citrate | 0.042 | 0.042 | 0.042 | 0.042 | 0.042 | 0.042 | 0.042 | 0.042 | 0.042 |
| | Total | 100 | 100 | 100 | 100 | 100 | 100 | 100 | 100 | 100 |
| (F) | Total amount of water | 96.05 | 95.85 | 95.55 | 94.05 | 93.85 | 93.55 | 92.05 | 91.35 | 91.55 |
| (C) | Total amount of propylene glycol | 3.00 | 3.00 | 3.00 | 5.00 | 5.00 | 5.00 | 7.00 | 7.00 | 7.00 |
| | (A)/(B) | 1.00 | 1.00 | 1.00 | 1.00 | 1.00 | 1.00 | 1.00 | 1.00 | 1.00 |
| | (D)/(A) | 10.0 | 14.0 | 20.0 | 10.0 | 14.0 | 20.0 | 10.0 | 14.0 | 20.0 |
| | (D)/((A) + (G)) | 1.4 | 2.0 | 2.9 | 1.4 | 2.0 | 2.9 | 1.4 | 2.0 | 2.3 |
| | (C)/(A) | 60 | 60 | 60 | 100 | 100 | 100 | 140 | 140 | 140 |
| | Evaluation of appearance | A | A | A | A | A | A | A | A | A |
| | Evaluation of flavor | A | A | A | A | A | A | A | A | A |

*1 and *2 The same as those shown in Table 1

TABLE 6

| | Component (% by mass) | Comparative Example 7 | Comparative Example 8 | Comparative Example 9 | Comparative Example 10 | Comparative Example 11 |
|---|---|---|---|---|---|---|
| (A) | β-Glycyrrhetinic acid | 0.01 | 0.03 | 0.01 | 0.03 | 0.05 |
| (B) | Cetylpyridinium chloride | 0.05 | 0.05 | 0.05 | 0 | 0.01 |
| (C) | Propylene glycol | 3 | 3 | 1 | 3 | 3 |
| (D) | Polyoxyethylene hydrogenated castor oil (40EO) *1 | 0.2 | 0.2 | 0.5 | 0.5 | 0.5 |
| (G) | dl-α-Tocopherol acetate | 0.1 | 0.1 | 0.1 | 0.1 | 0.1 |
| | Flavor *2 | 0.2 | 0.2 | 0.2 | 0.2 | 0.2 |
| | Glycerin | 0 | 10 | 0 | 0 | 0 |
| (E) | Citric acid | 0.008 | 0.008 | 0.008 | 0.008 | 0.008 |
| | Sodium citrate | 0.042 | 0.042 | 0.042 | 0.042 | 0.042 |
| | Total | 100 | 100 | 100 | 100 | 100 |
| (F) | Total amount of water | 96.39 | 86.37 | 98.09 | 96.12 | 96.09 |
| (C) | Total amount of propylene glycol | 3.00 | 3.00 | 1.00 | 3.00 | 3.00 |
| | (A)/(B) | 0.20 | 0.60 | 0.20 | — | 5.00 |
| | (D)/(A) | 20.0 | 6.7 | 50.0 | 16.7 | 10.0 |
| | (D)/((A) + (G)) | 0.6 | 0.6 | 1.6 | 1.5 | 1.4 |
| | (C)/(A) | 300 | 100 | 100 | 100 | 60 |

TABLE 6-continued

| Component (% by mass) | Comparative Example 7 | Comparative Example 8 | Comparative Example 9 | Comparative Example 10 | Comparative Example 11 |
|---|---|---|---|---|---|
| Evaluation of appearance | C | C | C | C | C |
| Evaluation of flavor | B | C | C | C | B |

*[1] and *[2] The same as those shown in Table 1

TABLE 7

| | Component (% by mass) | Example 31 | Example 32 |
|---|---|---|---|
| (A) | β-Glycyrrhetinic acid | 0.03 | 0.03 |
| (B) | Cetylpyridinium chloride | 0.05 | 0.05 |
| (C) | Propylene glycol | 3 | 3 |
| (D) | Polyoxyethylene hydrogenated castor oil (40EO) *[1] | 0.5 | 0.5 |
| (G) | dl-α-Tocopherol acetate | 0.1 | 0.1 |
| | Flavor *[4] | 0.2 | |
| | Flavor *[5] | | 0.2 |
| | Glycerin | 0 | 0 |
| (E) | Citric acid | 0.008 | 0.008 |
| | Sodium citrate | 0.042 | 0.042 |
| | Total | 100 | 100 |
| (F) | Total amount of water | 96.07 | 96.07 |
| (C) | Total amount of propylene glycol | 3.00 | 3.01 |
| | (A)/(B) | 0.60 | 0.60 |
| | (D)/(A) | 16.7 | 16.7 |
| | (D)/((A) + (G)) | 3.8 | 1.5 |
| | (C)/(A) | 100 | 100 |
| | Evaluation of appearance | A | A |
| | Evaluation of flavor | A | A |

*[1] The same as that shown in Table 1
*[4] The flavor shown in Table 9
*[5] The flavor shown in Table 10

TABLE 8

| Peppermint oil | 15 |
|---|---|
| Spearmint oil | 10 |
| Eucalyptus oil | 8 |
| Menthol | 40 |
| Methyl salicylate | 5 |
| Cinnamic aldehyde | 0.7 |
| Cinnamon oil | 0.3 |
| Anethole | 5 |
| Anisaldehyde | 5 |
| Benzaldehyde | 0.5 |
| Camphor | 4 |
| Rose oil | 1.5 |
| Nutmeg oil | 0.5 |
| Lactone C-10 | 0.1 |
| Eugenol | 1 |
| Thyme oil | 1 |
| Funnel oil | 0.4 |
| Propylene glycol | 2 |
| Total | 100 |

TABLE 9

| Peppermint oil | 20 |
|---|---|
| Spearmint oil | 5 |
| Eucalyptus oil | 10 |
| Mentha oil | 2 |
| Menthol | 40 |
| Methyl salicylate | 3 |
| Cinnamon oil | 1 |
| Anethole | 10 |
| Carvone | 1 |
| Clove oil | 0.5 |
| Camphor | 2 |
| Sage clary oil | 0.5 |
| Juniper berry oil | 1 |
| Petitgrain oil | 0.1 |
| Coriander oil | 0.1 |
| Neroli oil | 0.2 |
| Nutmeg oil | 0.5 |
| Basil oil | 0.1 |
| Lactone C-10 | 0.1 |
| Eugenol | 0.5 |
| Thyme oil | 0.5 |
| Thymol | 0.2 |
| Rosemary oil | 0.1 |
| Pimento berry oil | 0.1 |
| Ginger oil | 0.1 |
| Funnel oil | 0.4 |
| Propylene glycol | 1 |
| Total | 100 |

TABLE 10

| Peppermint oil | 15 |
|---|---|
| Spearmint oil | 5 |
| Eucalyptus oil | 8 |
| Menthol | 40 |
| Anethole | 8 |
| Camphor | 1 |
| Orange oil | 5 |
| Lemon oil | 2 |
| Grapefruit oil | 5 |
| Mandarin oil | 1.5 |
| Lime oil | 0.5 |
| Petitgrain oil | 0.5 |
| Clove oil | 0.5 |
| Cassia oil | 0.1 |
| Lemon grass oil | 0.5 |
| Melissa oil | 0.1 |
| Coriander oil | 0.1 |
| Nutmeg oil | 0.5 |
| Basil oil | 0.1 |
| Rose oil | 2 |
| Lactone C-10 | 0.1 |
| Lactone C-12 | 0.1 |
| Eugenol | 0.5 |
| Thyme oil | 0.5 |
| Thymol | 0.2 |
| Palmarosa oil | 0.1 |
| Vanillin | 0.1 |
| Propylene glycol | 3 |
| Total | 100 |

As shown in Tables 5 to 7, when compared with the mouth wash liquids of Comparative Examples 7 and 8, in which the content of the component (D) was less than 0.4% by mass, Comparative Example 9, in which the content of the component (C) was less than 2% by mass, Comparative Example 10, which did not contain the component (B), and Comparative Example 11, in which the mass ratio between the component (A) and the component (B) was more than 1.3, the mouth wash liquids of Examples 13 to 32 were found to have stable transparency and to provide a good flavor.

The invention claimed is:

1. A method for producing a mouth wash formulation, comprising:
    blending from 80 to 97% by mass water (F) with from 0.02 to 0.2% by mass of an organic acid and a salt thereof (E) to adjust the pH of a resultant mixture at 25° C. to from 5 to 6.8, thereby obtaining a mixture comprising the component (F) and the component (E),
    blending from 0.03% by mass to 0.07% by mass of cetylpyridinium chloride (B) into the mixture comprising the component (F) and the component (E), thereby obtaining a mixture comprising the component (F), the component (E), and the component (B),
    blending from 0.02% by mass to 0.08% by mass of β-glycyrrhetinic acid (A) and from 3% by mass to 8% by mass of propylene glycol (C) into the mixture comprising the component (F) and the component (E), thereby obtaining a mixture comprising the component (F), the component (E), the component (A), and the component (C),
    blending from 0.4% by mass to 1% by mass of polyoxyethylene hydrogenated castor oil (D) into the mixture comprising the component (F) and the component (E), thereby obtaining a mixture comprising the component (F), the component (E), and the component (D), and
    blending from 2% by mass to 7% by mass of polyol selected from the group consisting of glycerin, sorbitol, and mixtures thereof, and from 1% by mass to 5% by mass of ethanol to a mixture comprising the component (A), the component (B), the component (C), the component (D), the component (E) and the component (F), wherein
    a mass ratio between the component (A) and the component (B), (A)/(B), is from 0.3 to 1.3,
    after completion of the blending of the component (F) with the component (E), the blending of the component (B), the component (A), and the component (C) is simultaneous, or
    the blending of the component (B) is followed by the blending of both the component (A) and component (C), and
    the blending of the component (D) is carried out before, simultaneously with, or after the blending of the component (B), and the blending of the component (D) is carried out before or after the blending of the component (A) and component (C),
    wherein percentages by mass are relative to the mass of the mouth wash formulation,
    wherein said organic acid is selected from the group consisting of citric acid, lactic acid, and malic acid.

2. The method for producing a mouth wash formulation according to claim 1, wherein the blending of the component (D) and the blending of the component (B) are simultaneously carried out, or the blending of the component (B) is carried out, followed by blending of the component (D).

3. The method for producing a mouth wash formulation according to claim 1, wherein an amount of the component (F) is from 70% by mass to 97% by mass.

4. The method for producing a mouth wash formulation according to claim 1, wherein a mass ratio between the component (D) and the component (A), (D)/(A), is from 8 to 35.

5. The method for producing a mouth wash formulation according to claim 1, wherein:
    the mouth wash formulation comprises an oily component (G) other than surfactants,
    the component (G) is a component other than the component (D) and the component (A), and
    a mass ratio between an amount of the component (D) and a total amount of the component (A) and the component (G), (D)/((A)+(G)), is from 0.8 to 4.

6. The method for producing a mouth wash formulation according to claim 1, wherein a mass ratio between the component (C) and the component (A), (C)/(A), is from 40 to 400.

7. The method for producing a mouth wash formulation according to claim 1, wherein an amount of surfactants other than the component (D) is 0.2% by mass or less.

8. The method for producing a mouth wash formulation according to claim 1, wherein a mass ratio between the component (C) and the component (A), (C)/(A), is from 50 to 250.

9. The method for producing a mouth wash formulation according to claim 1, wherein an amount of glycerin is 5% by mass or less.

10. The method for producing a mouth wash formulation according to claim 1, wherein an amount of nonionic surfactants other than the component (D) is 0.05% by mass or less.

11. The method for producing a mouth wash formulation according to claim 1, wherein the amount of propylene glycol (C) is 3 to 7%.

12. The method for producing a mouth wash formulation according to claim 1, wherein the amount of polyoxyethylene hydrogenated castor oil (D) is 0.4 to 0.7%.

13. The method for producing a mouth wash formulation according to claim 1, wherein the organic acid is citric acid.

* * * * *